United States Patent [19]

Shroot et al.

[11] Patent Number: 4,940,696
[45] Date of Patent: Jul. 10, 1990

[54] BENZONAPHTHALENE DERIVATIVES AND THEIR USE IN THERAPEUTIC AND COSMETIC COMPOSITIONS

[75] Inventors: Braham Shroot, Antibes; Jacques Eustache, Crasse; Jean-Michel Bernardon, Nice, all of France

[73] Assignee: Centre International de Recherches Dermatologioues (CIRD), Valbonne, France

[21] Appl. No.: 120,958

[22] Filed: Nov. 16, 1987

Related U.S. Application Data

[62] Division of Ser. No. 850,145, Apr. 10, 1986, Pat. No. 4,717,720.

[30] Foreign Application Priority Data

Apr. 11, 1985 [LU] Luxembourg .................... 85849

[51] Int. Cl.⁵ ................ A61K 31/045; A61K 31/085; A61K 31/16; A61K 31/19; C07H 19/00; C07H 21/00; C07H 5/04; C07H 5/06; C07C 69/76; C07C 63/34; C07C 33/36; C07C 103/28

[52] U.S. Cl. ..................................... 514/62; 514/319; 514/423; 514/730; 514/859; 514/863; 514/885; 514/886; 514/880; 514/887; 514/912; 514/42; 514/43; 514/63; 514/532; 514/533; 514/543; 514/546; 514/547; 514/548; 514/549; 514/550; 514/551; 514/569; 514/617; 514/618; 514/621; 514/622; 514/237.5; 514/255; 546/14; 546/205; 548/406; 548/539; 560/56; 560/89; 560/90; 560/91; 560/100; 560/194; 560/250; 560/251; 560/252; 560/255; 536/18.7; 536/22; 556/419; 556/437; 556/449; 562/467; 562/490; 564/162; 564/169; 564/172; 564/173; 568/808; 544/64; 544/176; 544/225; 544/391

[58] Field of Search ..................... 556/419, 437, 449; 536/22, 18.7; 564/162, 169, 172, 173; 560/250, 251, 252, 255, 56, 89, 90, 91, 100, 194; 562/467, 490; 514/546, 547, 548, 549, 550, 551, 532, 533, 543, 42, 62, 63, 43, 569, 617, 618, 621, 622; 568/808

[56] References Cited
PUBLICATIONS
Chem. Abstracts: vol. 103; 160190k, (1985).

*Primary Examiner*—Mary C. Lee
*Assistant Examiner*—J. Richter
*Attorney, Agent, or Firm*—Cushman, Darby & Cushman

[57] ABSTRACT

A benzonaphthalene compound has the formula

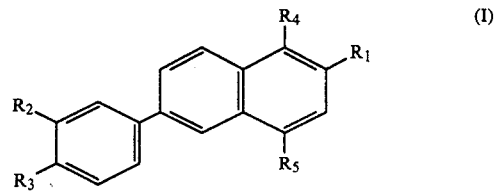

wherein $R_1$ represents

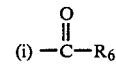

or (ii) —CH$_2$OH; $R_6$ represents

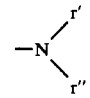

or OR$_7$ wherein R$_7$ represents hydrogen, alkyl having 1–20 carbon atoms, monohydroxyalkyl or polyhydroxyalkyl, r' or r" represent hydrogen, lower alkyl, mono or polyhydroxyalkyl, aryl or a residue of an amino acid or a sugar, or together form a heterocycle; R$_2$ represents hydrogen, alkyl having 1–15 carbon atoms, alkoxy having 1–4 carbon atoms or a cycloaliphatic radical; R$_3$ represents hydrogen, hydroxy, alkyl having 1–4 carbon atoms, alkoxy having 1–10 carbon atoms, a cycloaliphatic radical, a thiocycloaliphatic radical or —O—Si(CH$_3$)$_2$—R$_8$ wherein R$_8$ represents lower alkyl; and R$_4$ and R$_5$ represent hydrogen, lower alkyl, hydroxy or lower acyloxy.

This compound is useful in the topical and systemic treatment of dermatologic diseases and in the treatment of the degeneration of conjunctive tissues. The compound also possesses anti-tumor acitivity.

18 Claims, No Drawings

BENZONAPHTHALENE DERIVATIVES AND THEIR USE IN THERAPEUTIC AND COSMETIC COMPOSITIONS

This is a division of application Ser. No. 850,145, filed Apr. 10, 1986, now U.S. Pat. No. 4,717,720.

The present invention relates to benzonaphthalene derivatives, to a process for preparing them and to their use in therapeutic and cosmetic compositions.

These new benzonaphthalene derivatives are usefully employed in the topical and systemic treatment of dermatological diseases linked to keratinization disorders (differentiation-proliferation) and dermatological diseases, or others, with inflammatory and/or immunoallergic components and in the treatment of diseases attributable to the degeneration of conjuctive tissue. The benzonaphthalene derivatives of the present invention also exhibit anti-tumor activity. Moreover, these derivatives can be employed in the treatment of atopy be it cutaneous or respiratory.

The benzonaphthalene derivatives of the present invention are also usefully employed in the field of ophthalmology and principally in the treatment of corneopathies.

A number of compounds have already been proposed for the various treatments noted above and principally compounds known under the designation of "retinoids" of which the most well-known ones are the trans and cis retinoic acids (tretinoin and isotretinoin) and etretinate.

Compared to these known compounds, the benzonaphthalene derivatives according to the present invention exhibit a strong activity and better stability to light and to oxygen of the air.

The benzonaphthane derivatives of the present invention can be represented by the following formula:

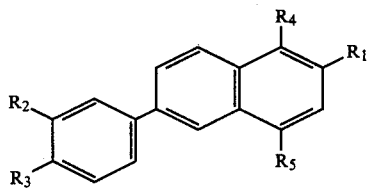

wherein
$R_1$ represents:

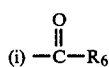

$R_6$ represents

or $-OR_7$ wherein $R_7$ represents hydrogen, alkyl having 1-20 carbon atoms, monohydroxyalkyl or polyhydroxyalkyl, r' and r" represent hydrogen, lower alkyl, mono- or polyhydroxyalkyl, aryl optionally substituted or a residue of an amino acid or aminated sugar or r' and r" taken together form a heterocycle, $R_2$ represents hydrogen, branched or straight chain alkyl having 1-15 carbon atoms, alkoxy having 1-4 carbon atoms or a cycloaliphatic group, $R_3$ represents hydrogen, hydroxy, straight or branched chain alkyl having 1-4 carbon atoms, alkoxy having 1-10 carbon atoms, a cycloaliphatic group substituted or not, a thio-cycloaliphatic group or a group of the formula $-O-Si(CH_3)_2-R_8$ wherein $R_8$ represents linear or branched lower alkyl, $R_4$ and $R_5$ each independently represent hydrogen, lower alkyl, hydroxy or a lower acyloxy group, and the salts of the said benzonaphthalene derivatives of Formula I.

By the expression "lower alkyl" is meant alkyl radicals having from 1-6 carbon atoms and principally methyl, ethyl, isopropyl, butyl and tert.butyl.

The term "alkoxy" is intended to include radicals having 1-10 carbon atoms and principally methoxy, ethoxy, isopropoxy, hexyloxy and decyloxy radicals.

By the expression "lower acyloxy" is meant radicals having 1-4 carbon atoms and principally acetyloxy and propionyloxy radicals.

By the term "monohydroxyalkyl" is meant a monohydroxy substituted radical having 2 or 3 carbon atoms, principally, 2-hydroxy ethyl and 2-hydroxypropyl.

Representative residues of aminated sugars include those derived from glucosamine, galactosamine and mannosamine.

By the term "polyhydroxyalkyl" is meant an alkyl radical having 3-6 carbon atoms substituted 2-5 hydroxyl groups, such as 2,3-dihydroxy propyl, 1,3-dihydroxy propyl, or the residue of pentaerythritol.

The term "cycloaliphatic" is meant to include a mono or polycyclic radical such as, for example, 1-methyl cyclohexyl or 1-adamantyl.

The preferred thiocycloaliphatic radical is, principally, 1-adamantylthio.

When r' and r" together form a heterocycle, it is preferably a piperidino, piperazino, morpholino or pyrrolidino radical.

The preferred compounds of Formula I are more particularly those having the following formula:

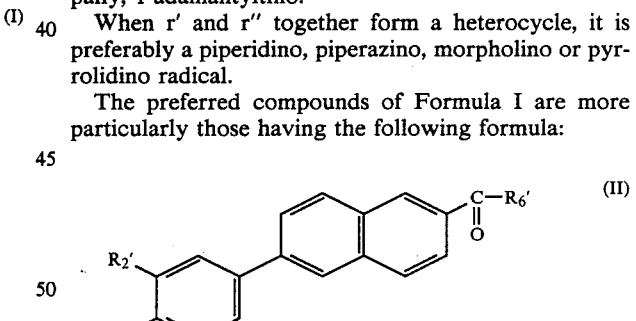

wherein
$R'_6$ represents

or $-OR'_7$,
r' and r" each independently represent hydrogen or lower alkyl, or r' and r" taken together form a morpholino radical,
$R'_7$ represents hydrogen or lower alkyl,
$R'_2$ represents hydrogen, alkyl, alkoxy or 1-adamantyl, and R'₃ represents hydrogen, hydroxy, alkyl, alkoxy or 1-adamantylthio.

Representative compounds of the present invention include:

(1) 6-(3-methylphenyl)-2-naphthoic acid and its methyl ester,
(2) 6-(4-tert.butyl phenyl)-2-naphthoic acid and its methyl ester,
(3) 6-(3-tert.butyl phenyl)-2-naphthoic acid and its methyl ester,
(4) 6-(3,4-dimethoxy phenyl)-2-naphthoic acid and its methyl ester,
(5) 6-[p-(1-admantylthio)phenyl]-2-naphthoic acid and its methyl ester,
(6) 6-[3-(1-adamantyl)-4-methoxyphenyl]-2-naphthoic acid and its methyl ester,
(7) the methyl ester of 6-[3-(1-adamantyl)-4-tert.butyl-dimethylsilyloxyphenyl]-2-naphthoic acid,
(8) the methyl ester of 6-[3-(1-adamantyl)-4-hydroxyphenyl]-2-naphthoic acid,
(9) 6-[3-(1-adamantyl-4-hydroxyphenyl]-2-naphthoic acid,
(10) the methyl ester of 6-[3-(1-adamantyl)-4-decyloxyphenyl]-2-naphthoic acid,
(11) 6-[3-(1-adamantyl)-4-decyloxyphenyl]-2-naphthoic acid,
(12) the methyl ester of 6-[3-(1-adamantyl)-4-hexyloxyphenyl]-2-naphthoic acid,
(13) 6-[3-(1-adamantyl)-4-hexyloxyphenyl]-2-naphthoic acid,
(14) the methyl ester of 6-[3-(1-adamantyl)-4-methoxyphenyl]-4-acetoxy-1-methyl-2-naphthoic acid,
(15) 6-[3-(1-adamantyl)-4-methoxyphenyl]-4-hydroxy-1-methyl-2-naphthoic acid,
(16) the methyl ester of 6-[3-(1-adamantyl)-4-methoxyphenyl]-4-hydroxy-1-methyl-2-naphthoic acid,
(17) the methyl ester of 6-[3-(1-adamantyl)-4-methoxyphenyl]-1-methyl-2-naphthoic acid,
(18) 6-[3-(1-adamantyl)-4-methoxyphenyl]-1-methyl-2-naphthoic acid,
(19) 6-[3-(1-adamantyl)-4-methoxyphenyl]-2-naphthalene methanol,
(20) the ethylamide of 6-[3-(1-adamantyl)-4-methoxyphenyl]-2-naphthoic acid,
(21) the morpholide of 6-[3-(1-adamantyl)-4-methoxyphenyl]-2-naphthoic acid,
(22) the methyl ester of 6-[3-tert.butyl-4-methoxyphenyl]-2-naphthoic acid,
(23) 6-(3-tert.butyl-4-methoxyphenyl)-2-naphthoic acid,
(24) the methyl ester of 6-[3-(1,1-dimethyldecyl)-4-methoxyphenyl]-2-naphthoic acid, and
(25) 6-[3-(1,1-dimethyldecyl)-4-methoxyphenyl]-2-naphthoic acid.

The present invention also relates to a process for preparing the compounds of Formula I.

According to this process the compounds of Formula I are obtained by a coupling reaction between a halogenated compound of Formula III and a halogenated derivative of naphthalene of Formula IV:

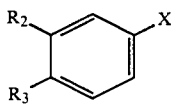
(III)

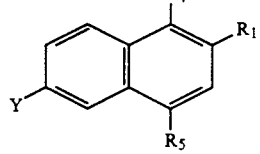
(IV)

wherein
R₁ to R₅ have the same meanings as those given above for Formula I and
X and Y represent Cl, Br, F or I.

According to this coupling reaction, the halogenated compound of Formula III is transformed into its magnesium, lithium or zinc form in accordance with methods described in the literature and is coupled with the halogenated naphthalene derivative of Formula IV by employing, as a reaction catalyst, a transition metal or one of its complexes.

Particularly preferred catalysts are those derived from nickel or palladium and more particularly the compounds of Ni$_{II}$ (NiCl₂) with various phosphines.

The coupling reaction is generally carried out at a temperature between −20° and +30° C. in an anhydrous solvent such as, for example, dimethylformamide or tetrahydrofuran.

The resulting product can be purified by recrystallization or silica column chromatography.

Obviously, the choice of the halogenated naphthalene derivative of Formula IV, for use in the coupling reaction with the halogenated compound of Formula III, must be such that it can lead, by subsequent reaction, to the various meanings of the R₁ radical given above.

When the compounds according to the present invention are provided in salt form, it is a question of salts of an alkali or alkaline earth metal or of an organic amine when the compounds have at least one free acid function.

The present invention also relates to a medicinal composition comprising as the active principle thereof the compounds of Formula I as defined above.

These compounds exhibit excellent activity in the test for inhibiting ornithine decarboxylase after induction, by "tape stripping" the body of a nude rat. This test is considered a measure of the activity of the retinoids with regard to cellular proliferation phenomenon.

For instance, it has been noted that in this test, 6-[3-(1-adamantyl)-4-methoxyphenyl]-2-naphthoic acid exhibits an effective dose between 5 and 25 nmoles applied per cm².

The compounds according to the invention also exhibit a strong activity in the differentiation test of embryonic tetracarcinoma F9 rat cells (Cancer Research 43, page 5268, 1983).

As an illustration, 6-[3-(1-adamantyl)-4-methoxyphenyl]-2-naphthoic acid, at a 0.01 micromolar concentration induces the differentiation of F9 carcinoma cells in endoderm cells.

6-(3-tert.butyl phenyl)-2-naphthoic acid acts in the same fashion at a concentration of 1 micromolar.

Moreover, the irritation test carried out on a rabbit has shown that the compounds of Formula I are less irritating than known retinoids of analogous structure. Moreover, their acute toxicity is weaker.

The compounds of the present invention are indeed particularly suitable for the treatment of dermatological diseases linked to a keratinization disorder (differentiation, proliferation), as well as dermatological diseases or others with inflammatory and/or immunoallergic components such as principally:

acne vulgaris, comedons or polymorphs, solar acne seniles and medicamental or professional acne;

extensive and/or severe forms of psoriasis, and other keratinization disorders, and principally ichtyosis and ichtyosiform states;

Darier disease;

palmo-plantary keratodermy;

leucoplasies and leucoplasiform states, lichen plan;

all dermatological proliferations, benign or malignant, severe or extended.

They are also active for certain rheumatic diseases principally psoriasic rheumatism, for cutaneous or respiratory atopies, as well as for certain ophthalmologic disorders relative to the corneopathies.

The present invention also relates to medicinal compositions containing at least one compound of Formula I, as defined above and/or a salt thereof.

The present invention thus relates to a new medicinal composition, intended principally for the treatment of the above-mentioned diseases, comprising in a pharmaceutically acceptable support, at least one compound of Formula I and/or a salt thereof.

As has been indicated previously, the benzonaphthalene derivatives according to the present invention, relative to known retinoids, exhibit better stability against light and oxygen, this being essentially due to the fact that they do not possess any easily isomerized double bonds.

The compounds according to the present invention are generally administered at a daily dosage of about 2 μg/kg to 2 mg/kg of body weight.

As vehicles or supports for these compositions, there can be employed any conventional support, the active compound being found either in the dissolved state or in the dispersed state in the vehicle or support.

The composition can be administered enterally, parenterally, topically or ocularly. When administered enterally, the medicinal composition can be provided in the form of tablets, gelules, lozenges, syrups, suspension, solutions, powders, granules or emulsions. When administered parenterally the medicinal composition can be provided in the form of solutions or suspensions for perfusion or injection.

When administered topically, the pharmaceutical compositions based on the compounds in accordance with the present invention can be provided in the form of ointments, tinctures, creams, pommades, powders, impregnated pads, buffers, solutions, lotions, gels, sprays or even suspensions.

These compositions for topical application or administration can be provided either under anhydrous form, or in aqueous form according to clinical indications. When administered ocularly, the compositions are principally eyewashes.

The topical or ocular composition contains preferably between 0.0005 and 5 weight percent of the active compound based on the total weight of the composition.

The compounds of Formula I, according to the present invention also find use in the cosmetic field, in particular in body and hair hygiene and principally for acne, hairgrowth, preventing hair fallout, to combat against the oily appearance of the skin or hair, in the protection against harmful effects of the sun or in the treatment of physiologically dry skin.

The present invention then also envisages a cosmetic composition containing in a cosmetically acceptable support at least one compound of Formula I and/or a salt thereof, this composition being provided principally in the form of a lotion, gel, soap or shampoo.

The concentration of the compound(s) of Formula I in the cosmetic compositions is between 0.0005 and 2 weight percent, preferably between 0.01 and 1 weight percent, based on the total weight of the composition.

The medicinal and cosmetic compositions according to the present invention can contain inert or even pharmacodynamic or cosmetically active adjuvants and principally: hydrating agents such as thiamorpholinone and its derivatives or urea; antiseborrheic agents such as S-carboxymethylcysteine, S-benzyl cysteamine and their derivatives, or tioxolone; antibiotics such as erythromycin, neomycin or the tetracyclines; agents favoring hair growth such as "Minoxidil" (2,4-diamino-6-piperidino-pyrimidine-3-oxide) and its derivatives, Diazoxide and Phenytoin; steroidal anti-inflammatory agents; carotenoids and principally $\beta$-carotene; and antipsoriasic agents such as anthralin and its derivatives, 5,8,11,14-eicosatetrainoic acid and 5,8,11-triynoic acid.

The compositions according to the present invention can also contain flavor improving agents, preservatives, stabilizers, humidity regulating agents, pH regulating agents, osmotic pressure modifying agents, emulsifiers, UV-A and UV-B filters and antioxidants such as $\alpha$-tocopherol, butylhydroxy anisole or butylhydroxy toluene.

The following non-limiting examples illustrate several examples for the preparation of the active compounds of Formula I according to the present invention, as well as examples of compositions containing these active compounds.

EXAMPLE 1

Methyl ester of 6-(3-methylphenyl)-2-naphthoic acid. Compound of Formula II wherein $R'_3=H$ and $R'_2=-CH_3$ and $R'_6=-OCH_3$ 342 mg (2 mmol) of 3-bromotoluene in 4 ml of THF are converted into the corresponding magnesium form and then treated with an equivalent of zinc chloride to provide the corresponding zinc derivative. There are successively added 310 mg (1.17 mmol) of methyl 6-bromo-2-naphthoate and 10 mg (0.02 mmol) of NiCl$_2$/1,2-(diphenylphosphino)ethane - DPPE - as the catalyst. The reaction mixture is stirred at ambient temperature for 30 minutes and the mineral salts are then removed by passing the reaction mixture through a 2×3 cm silica column. The reaction mixture is then evaporated to dryness and the residue is chromatographed (HPLC column - Zorbax sil), using as the eluant, a mixture of cyclohexane (75%) and ether (25%). The product thus recovered has an Rf=0.45 (silica plate, eluant: hexane 50%, dichloromethane 50%) and crystallizes on evaporation of the chromatography solvents. The yield is 84%. Melting point - 107° C.

EXAMPLE 2

Methyl ester of 6-(4-tert.butyl phenyl)-2-naphthoic acid. Compound of Formula II wherein $R'_2=H$, $R'_3=-C(CH_3)_3$ and $R'_6=-OCH_3$ In a manner analogous to Example 1, starting with 639 mg (3.0 mmol) of 4-bromo tert.butyl benzene and 465 mg (1.75 mmol) of methyl 6-bromo-2-naphthoate, 0.30 g of the expected product is obtained. Yield - 54%. Melting point - 154° C.

EXAMPLE 3

Methyl ester of 6-(3-tert.butyl phenyl)-2-naphthoic acid. Compound of Formula II wherein $R'_3=H$, $R'_2=-C(CH_3)_3$ and $R'_6=-OCH_3$ 3.50 g (16.4 mmol) of 3-tert.butyl bromobenzene are added to a suspension of magnesium (0.44 g - 18m Atg) in 20 ml of dry tetrahydrofuran. The reaction is initiated by addition of an iodine crystal and continued at 50° C. for 30 minutes.

2.46 g (18 mmol) of anhydrous zinc chloride dissolved in 20 ml of dry tetrahydrofuran are then added and after 15 minutes, the reaction mixture is cooled to 0° C. At this point, 3.63 g (13.7 mmol) of methyl 6-bromo-2-naphthoate and 86 mg (0.26 mmol) of the NiCl$_2$/DPPE complex are added to the reaction mixture.

After stirring for 1 hour at ambient temperature, 100 ml of water are added and the mixture is extracted with ether. After washing the organic phase with a saturated solution of sodium bicarbonate, and water, then drying (sodium sulfate) and evaporating the solvents, the resulting residue is recrystallized in heptane. 3.12 g of the methyl ester of 6-(3-tert.butyl phenyl)-2-naphthoic acid which melts at 138° C. are obtained.

EXAMPLE 4

6-(3-tert.butyl phenyl)-2-naphthoic acid. Compound of Formula II wherein $R'_3=H$, $R'_2=-C(CH_3)_3$ and $R'_6=OH$ 1.0 g (3.14 mmol) of the methyl ester of 6-(3-tert.butyl phenyl)-2-naphthoic acid obtained in Example 3 is added to a mixture of 95% ethanol (40 ml) and soda (4 ml, 5N).

The mixture is heated at 60° C. for 2 hours at which point 50 ml of water are added and the mixture is acidified to pH 1 with 2N HCl. The acidified mixture is then extracted with ether and the organic phase is washed with water until neutral. After drying (sodium sulfate) and evaporation of the solvent, 6-(3-tert.butyl phenyl)-2-naphthoic acid (900 mg) which sublimes at 190° C. is obtained.

EXAMPLE 5

Methyl ester of 6-[p-(1-adamantylthio)phenyl]-2-naphthoic acid

Compound of Formula II wherein $R'_2=H$, $R'_3=1$-adamantylthio and $R'_6=-OCH_3$ (a) p-(1-adamantylthio) bromobenzene 3.78 g (20 mmol) of p-bromothiophenol, 3.04 g (20 mmol) of 1-adamantanol and 10 ml of trifluoroacetic acid are stirred at ambient temperature for 8 hours and then poured into water. Sodium bicarbonate is added until the mixture is neutral at which time it is extracted with methylene chloride. The organic phase is dried and evaporated. After recrystallization in isooctane, 5.9 g of the expected product are obtained. Yield - 92%. Melting point: 121°-122° C.

(b) Methyl ester of 6-[p-(1-adamantylthio)phenyl]-2-naphthoic acid 0.64 g (26.5m Atg) of magnesium suspended in 10 ml of tetrahydrofuran (THF) are treated slowly with 5.7 g (17.6 mmol) of p-(1-adamantylthio) bromobenzene. After heating at reflux for 2 hours and cooling to 20° C., 2.4 g (17.6 mmol) of anhydrous Zn Cl$_2$ are added. The mixture is stirred for one hour at 20° C. at which point 2.8 g (10.4 mmol) of methyl 6-bromo-2-naphthoate are added and then 92 mg of NiCl$_2$/1,2-(diphenylphosphino)ethane-DPPE complex are added.

The mixture is stirred at ambient temperature for 2 hours, poured into water, extracted with methylene chloride, washed with sodium bicarbonate, dried and then evaporated. The residue is recrystallized in a mixture of diisopropyl oxide and ethyl acetate. 3.7 g of the expected product are obtained. Yield - 84%. Melting point: 189°-190° C.

EXAMPLE 6

6-[p-(1-adamantylthio)phenyl]-2-naphthoic acid. Compound of Formula II wherein $R'_2=H$, $R'_6=OH$ and $R'_3=1$-adamantylthio 3 g (7 mmol) of the ester obtained in Example 5(b) are treated with a solution of soda in methanol (150 ml, 5N). The reaction mixture is heated at reflux for 12 hours, evaporated, taken up in water and acidified with concentrated HCl. The resulting solid is filtered and dried under a vacuum on phosphoric anhydride. The resulting white solid is pulverized in methanol at reflux, cooled and filtered. 2.5 g of the expected product are thus obtained. Yield - 86%. Melting point: 334°-336° C.

EXAMPLE 7

Methyl ester of 6-(3,4-dimethoxy phenyl)-2-naphthoic acid. Compound of Formula II wherein $R'_2=R'_3=R'_6=-OCH_3$ 0.93 g (38.3 mAtg) of magnesium in 20 ml of THF are slowly treated with 5.5 g (25.5 mmol) of 4-bromoveratrole. At the end of the addition, the mixture is heated at reflux for two hours, and then cooled. At this point 3.48 g (25.5 mmol) of anhydrous ZnCl$_2$ are added and the mixture is stirred one hour at ambient temperature. 3.98 g (15 mmol) of methyl 6-bromo-2-naphthoate are then added followed by the addition of 130 mg of NiCl$_2$/DPPE complex. The mixture is stirred for two hours at ambient temperature and then poured into water and extracted with dichloromethane. The organic phase is dried and evaporated. The residue is recrystallized in a mixture of isopropyl ether and ethyl acetate. 3.4 g of the expected product are obtained. Yield - 70%. Melting point: 147°-148° C.

EXAMPLE 8

6-(3,4-dimethoxyphenyl-2-naphthoic acid. Compound of Formula II wherein $R'_2=R'_3=-OCH_3$ and $R'_6=OH$ 2.6 g (8 mmol) of the ester obtained in Example 7 are treated with a solution of soda in methanol (200 ml, 2N). The reaction mixture is heated at reflux for 8 hours, evaporated, taken up in water, acidified with concentrated HCl, and filtered. The solid thus obtained is dried under a vacuum (on P$_2$O$_5$). The resulting white solid is pulverized in methanol at reflux, cooled and then filtered. 2.3 g of the expected product are obtained. Yield - 92%. Melting point: 241°-243° C.

EXAMPLE 9

Methyl ester of 6-[3-(1-adamantyl)-4-methoxy phenyl]-2-naphthoic acid. Compound of Formula II wherein R′$_3$—OCH$_3$, R′$_2$=1-adamantyl and R′$_6$=OCH$_3$ (a) 2-(1-adamantyl)-4-bromophenol 34.6 g (200 mmol) of p-bromophenol and 30.4 g (200 mmol) of 1-adamantanol are dissolved in 100 ml of dichloromethane. To the resulting solution there are slowly added 10 ml of concentrated sulfuric acid. The mixture is stirred for 8 hours at ambient temperature, poured into water, neutralized with sodium bicarbonate, extracted with methylene chloride, dried and evaporated. After recrystallization in isooctane 52.8 g of the expected product are obtained. Yield - 86%. Melting point: 140°-141° C.

(b) 2-(1-adamantyl)-4-bromoanisole

To a suspension of sodium hydride (80% in oil, 4.32 g, 144 mmol) in 50 ml of THF, there are slowly added, while maintaining the temperature at 20° C., 36.8 g (120 mmol) of 2-(1-adamantyl)-4-bromophenol. The mixture is stirred for 1 hour at ambient temperature at which point 9 ml (144 mmol) of methyl iodide are added. The mixture is then stirred for 2 hours at 20° C., poured into water, extracted with ether, dried and evaporated. The product is purified by passage through a silica column (10×30 cm), eluting with a mixture of hexane (90%) and dichloromethane (10%). On evaporation, 26.2 g of a white solid are obtained. Yield - 68%. Melting point: 138°-139° C.

(c) Methyl ester of 6-[3-(1-adamantyl)-4-methoxy phenyl]-2-naphthoic acid

To a suspension of magnesium (1.64 g, 67.5 m Atg) in 30 ml of THF, there is added a solution of 1.4 g (4.5 mmol) of 2-(1-adamantyl)-4-bromoanisole and 0.39 ml of dibromoethane in 10 ml of THF. The mixture is stirred until the reaction is initiated and then there is slowly added a solution of 13.1 g (40.8 mmol) of 2-(1-adamantyl)-4-bromoanisole in 90 ml of THF. The mixture is heated at reflux for 2 hours, and then cooled to 20° C. There are then added 6.2 g (45 mmol) of anhydrous ZnCl$_2$. The mixture is stirred for 1 hour at 20° C. at which point 7.95 g (30 mmol) of methyl 6-bromo-2-naphthoate are added followed by the addition of 300 g of NiCl$_2$/DPPE complex. The mixture is stirred again for 2 hours at 20° C., poured into water, extracted with CH$_2$Cl$_2$, dried and evaporated. The product is isolated by column chromatography, eluting with a mixture of heptane (70%) and dichloromethane (30%) and then recrystallized in ethyl acetate. 12.2 g of the expected product are obtained. Yield - 78%. Melting point: 222°-223° C.

EXAMPLE 10

6-[3-(1-adamantyl)-4-methoxy phenyl]-2-naphthoic acid

Compound of Formula II wherein R′$_3$=OCH$_3$, R′$_2$=1-adamantyl and R′$_6$=OH 10.5 g of the ester obtained in Example 9(c) are treated with a solution of soda in methanol (200 ml, 4.2N). The mixture is heated at reflux for 48 hours. The solvents are evaporated and the resulting residue is taken up in water and acidified with concentrated HCl. The solid is filtered and dried under a vacuum over phosphoric anhydride.

The resulting white solid is recrystallized in a mixture of THF and ethyl acetate. 8.2. g of the expected product are obtained. Yield - 81%. Melting point: 325°-327° C.

EXAMPLE 11

Methyl ester of 6-[3-(1-adamantyl)-4-tert.butyl dimethylsilyloxylphenyl]-2-naphthoic acid Compound of Formula I wherein R$_4$=R$_5$=H, R$_2$=1-adamantyl, R$_3$=OSi(CH$_3$)$_2$C$_3$H$_7$ and

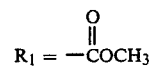

$$R_1 = -\overset{\overset{\displaystyle O}{\|}}{C}OCH_3$$

(a) 2-(adamantyl)-4-bromo-1-tert.butyldimethyl-silyloxybenzene 30.7 g of 2-adamantyl-4-bromophenol (100 mmol) are dissolved in DMF (200 ml). There are then added triethylamine (15.4 ml, 110 mmol) and 4-N,N-dimethylaminopyridine (DMAP, 500 mg, 4 mmol).

To the resulting solution there is slowly added a solution of tert.butyldimethylsilyl chloride (15.7 g, 104 mmol) in DMF (100 ml). The mixture is stirred at ambient temperature for 4 hours, poured into water, extracted with ether, dried (MgSO$_4$) and evaporated. The residue is dissolved in hexane and purified by passage through a silica column (eluant: hexane). 36.2 g (86%) of 2-adamantyl-4-bromo-1-tert.butyldimethylsilyloxy-benzene are obtained. Melting point: 111° C.

(b) Methyl ester of 6-[3-(1-adamantyl)-4-tert.butyl-dimethylsiloxyphenyl]-2-naphthoic acid 33.3 g (79 mmol) of the compound produced in part (a) above, dissolved in 200 ml of THF are slowly added to a suspension of magnesium (2.9 g, 118 Atg) in 60 ml of THF. Once the addition is complete, the mixture is heated at reflux for 2 hours at which point the temperature of the mixture is permitted to return to ambient temperature. 10.8 g (79 mmol) of anhydrous zinc chloride are added and the mixture is stirred for one hour at ambient temperature, at which point 10.5 g (39.5 mmol) of methyl 6-bromo-2-naphthoate and 500 mg of NiCl$_2$/DPPE complex are added. This mixture is then stirred for 2 hours at ambient temperature, poured into water, extracted with CH$_2$Cl$_2$, dried and evaporated. The residue is chromatographed on a silica column (eluant: mixture of heptane (70%) and ether (30%). 18.5 (90%) of the methyl ester of 6-[3-(1-adamantyl)-4-tert-.butyldimethylsilyloxyphenyl]-2-naphthoic acid are obtained. Melting point: 152°-153° C.

EXAMPLE 12

Methyl ester of 6[3-(1-adamantyl)-4-hydroxyphenyl]-2-naphthoic acid

Compound of Formula I wherein R$_4$=R$_5$=H, R$_2$=1-adamantyl, R$_3$=OH and R$_1$=COOCH$_3$ 17.5 g (33 mmol) of the ester produced in Example 11 are dissolved in 300 ml of THF. To this solution there is added 36.6 ml of a molar solution of tetrabutylammonium fluoride in THF. The mixture is stirred for 2 hours at ambient temperature, poured into water and extracted with CH$_2$Cl$_2$. The organic phase is recovered, dried (MgSO$_4$), and the solvents evaporated. The resulting residue is recrystallized in a mixture of ethylacetate (70%) and THF (30%) to give the expected ester. 11 g (81%). Melting point: 266° C.

EXAMPLE 13

6-[3-(1-adamantyl)-4-hydroxyphenyl]-2-naphthoic acid

Compound of Formula I wherein $R_4=R_5=H$, $R_2=$ 1-adamantyl, $R_3=OH$ and $R_1=COOH$ 5 g (12 mmol) of the ester obtained in Example 12 are treated with 200 ml of methanolic soda (2N), under nitrogen, for 8 hours. The solvents are evaporated and the residue taken up in water and acidified to pH 1 (concentrated HCl). The reaction mixture is filtered, washed with water, the solid product is extracted with ethyl ether, dried (MgSO$_4$) and evaporated. The residue is recrystallized in isopropylether, yielding 3.8 g (79%) of the expected acid. Melting point: 270°–271° C.

EXAMPLE 14

Methyl ester of 6-[3-(1-adamantyl)-4-decyloxyphenyl]-2-naphthoic acid

Compound of Formula I wherein $R_4=R_5=H$, $R_2=$ 1-adamantyl, $R_3=$—$OC_{10}H_{21}$ and $R_1=COOCH_3$ (a) 2-(1-adamantyl)-4-bromo-1-decyloxy benzene To a suspension of sodium hydride (80% in oil, 3.2 g, 104 mmol) in 100 ml of THF, there is slowly added a solution of 2-(1-adamantyl)-4-bromophenol (29 g, 95 mmol) in 200 ml of THF. The mixture is stirred until the evolution of gas ceases at which point 27.8 g (23 ml, 104 mmol) of 1-iododecane and 100 ml of DMF are added. The mixture is stirred for 12 hours at ambient temperature, poured into water, extracted with ether, dried and the solvents evaporated. The resulting residue is purified by passage through a silica column (eluant: heptane), yielding 40.7 g (96%) of 2-(1-adamantyl)-4-bromo-1-decyloxybenzene. Melting point: 69°–70° C.

(b) Methyl ester of 6-[3-(1-adamantyl)-4-decyloxyphenyl]-2-naphthoic acid

In a manner analogous to Example 9c, starting with 17.9 g (40 mmol) of the brominated derivative obtained in part (a) above, and 5.3 g of methyl 6-bromo-2-naphthoate, 7.4 g (67%) of the expected ester are obtained. Melting point: 113°–114° C.

EXAMPLE 15

6-[3-(1-adamantyl)-4-decyloxyphenyl]-2-naphthoic acid

Compound of Formula I wherein $R_4=R_5=H$, $R_2=$ 1-adamantyl, $R_3=$—$OC_{10}H_{21}$ and $R_1=COOH$ 6.3 g (11 mmol) of the ester obtained in Example 14 dissolved in 200 ml of THF are treated at reflux with 200 ml of 2M methanolic soda for 4 hours. The solvents are evaporated and the residue is taken up in water, acidified to pH 1 (concentrated HCl), filtered, washed with water and the solid is extracted with ether. The extract is dried and the solvent evaporated. The resulting residue is treated with 700 ml of ethyl acetate at reflux. On cooling 5.9 g (97%) of the expected acid are obtained. Melting point: 214°–215° C.

EXAMPLE 16

Methyl ester of 6-[3-(1-adamantyl)-4-hexyloxyphenyl]-2-naphthoic acid

Compound of Formula I wherein $R_4=R_5=H$, $R_2=$ 1-adamantyl, $R_3=$—$OC_6H_{13}$ and $R_1=$—$COOCH_3$ 5.3 g (13 mmol) of the ester obtained in Example 12 are dissolved in 100 ml of DMF and added to a suspension of NaH (80% in oil; 0.46 g; 15.4 mmol) in DMF (50 ml). The mixture is stirred at ambient temperature until the evolution of gas ceases, at which point 1-iodohexane (3.26 g; 2.3 ml; 15.4 mmol) is added. This mixture is then stirred for 4 hours at ambient temperature, poured into water, extracted with ether, dried and evaporated. The residue is purified by passage through a silica column (eluant: mixture of dichloromethane - 50% and hexane - 50%), then recrystallized in isooctane to give 5.5 g (87%) of the expected pure product. Melting point: 129°–130° C.

EXAMPLE 17

6-[3-(1-adamantyl)-4-hexyloxyphenyl]-2-naphthoic acid

Compound of Formula I wherein $R_4=R_5=H$, $R_2=$ 1-adamantyl, $R_3=$—$OC_6H_{13}$ and $R_1=$—$COOH$ In a manner analogous to Example 15, starting with 4.2 g (8.4 mmol) of the ester obtained in Example 16, 3.8 g (95%) of 6-[(1-adamantyl)-4-hexyloxyphenyl]-2-naphthoic acid are obtained. Melting point: 260°–261° C.

EXAMPLE 18

Methyl ester of 6-[3-(1-adamantyl)-4-methoxyphenyl]-4-acetoxy-1-methyl-2-naphthoic acid Compound of Formula I wherein $R_4=CH_3$, $R_5=$—$OCOCH_3$, $R_2=$ 1-adamantyl, $R_3=$—$OCH_3$ and $R_1=$—$COOCH_3$ 47.6 g (148 mmol) of 2-(1-adamantyl)-4-bromoanisole and 13.9 g (6.3 ml, 74 mmol) of dibromoethane, dissolved in 100 ml of THF are added slowly to a suspension of magnesium (5.4 g, 222 mmol) in the THF (1000 ml). The mixture is brought to reflux for 2 hours at which point zinc chloride (20.2 g, 148 mmol) is added. The mixture is stirred for 1 hour and there are successively added 24.9 g (74 mmol) of methyl 4-acetoxy-6-bromo-1-methyl-2-naphthoate and 500 mg of NiCl$_2$/DPPE complex. This mixture is stirred for 8 hours at ambient temperature, poured into a saturated aqueous solution of ammonium chloride, extracted with CH$_2$Cl$_2$, dried and the solvents evaporated. The resulting residue is purified by passage through a silica column (eluant: mixture of hexane, 40%, and CH$_2$Cl$_2$, 60%). The resulting product is recrystallized in isopropyl ether, yielding 23.5 g (64%) of the expected ester. Melting point: 201°–202° C.

EXAMPLE 19

6-[3-(1-adamantyl)-4-methoxyphenyl]-4-hydroxy-1-methyl-2-naphthoic acid

Compound of Formula I wherein $R_4=CH_3$, $R_5=OH$, $R_2=$ 1-adamantyl, $R_3=OCH_3$ and $R_1=COOH$ 23 g (46 mmol) of the ester obtained in Example 18 are treated at reflux for 12 hours with 300 ml of methanolic soda (2N). The solvents are evaporated and the residue is taken up in water and acidified to pH 1 (concentrated HCl). The solid is filtered, washed with water, dissolved in ethyl ether, dried (MgSO$_4$) and evaporated. The resulting residue is recrystallized in ethyl acetate to give 18.7 g (92%) of the expected acid. Melting point: 281°–283° C.

EXAMPLE 20

Methyl ester of 6-[3-(1-adamantyl)-4-methoxyphenyl]-4-hydroxy-1-methyl-2-naphthoic acid Compound of Formula I wherein $R_4=CH_3$, $R_5=OH$, $R_2=$1-adamantyl, $R_3=OCH_3$ and $R_1=COOCH_3$ 17 g (38 mmol) of the acid obtained in Example 19 are treated for 12 hours at reflux with 200 ml of methanol containing 2 ml of sulfuric acid. The solvents are evaporated and the residue is taken up in water, extracted with ether, dried and evaporated. The residue is purified by passage through a silica column using as the eluant a 90:10 mixture of ether/THF. The product is recrystallized in ethyl acetate to obtain the expected pure ester-15 g (86%). Melting point: 272°-274° C.

EXAMPLE 21

Methyl ester of 6-[3-(1-adamantyl)-4-methoxyphenyl]-1-methyl-2-naphthoic acid

Compound of Formula I wherein $R_4=CH_3$, $R_5=H$, $R_2=$1-adamantyl, $R_3=OCH_3$ and $R_1=$—$COOCH_3$ (a) Methyl 6-[3-(1-adamantyl)-4-methoxyphenyl]-4-dimethylaminothiocarbonyloxy-1-methyl-2-naphthoate 4.56 g of the ester obtained in Example 20, dissolved in THF (100 ml) are slowly added to a suspension of sodium hydride (80% in oil, 360 mg, 12 mmol) in DMF (50 ml). The mixture is stirred for 1 hour at ambient temperature and then for 1 hour at 40° C. There are then added 1.75 g (14 mmol) of dimethylthiocarbamoyl chloride, and the mixture is stirred initially at ambient temperature for 2 hours and then at 40° C. for 2 hours. The reaction mixture is poured into water, extracted with ether, dried, and the solvents evaporated. The product is purified by passage through a silica column (eluant: $CH_2Cl_2$), yielding 4 g (74%) of the expected intermediate product. Melting point: 137°-138° C.

(b) Methyl 6-[3-(1-adamantyl)-4-methoxyphenyl]-4-dimethylcarbonythio-1-methyl-2-naphthoate 3.8 g (7 mmol) of the ester obtained above in part (a) are heated under nitrogen at 260° C. for 0.5 hour. The residue is taken up in methylene chloride and purified by passage through a silica column (eluant: $CH_2Cl_2$). The resulting gum is taken up in isopropyl ether, yielding 3.3 g (87%) of the desired intermediate. Melting point: 201°-202° C.

(c) Methyl ester of 6-[3-(1-adamantyl)-4-methoxyphenyl]-1-methyl-2-naphthoic acid The intermediate obtained above in part (b)-(11 g, 20 mmol) is dissolved in 500 ml of ethanol. 20 g of Raney nickel are added and the reaction mixture is heated at reflux for 4 hours. 20 g of nickel are then added and the mixture is heated again for 1 hour, at which point the mixture is cooled, concentrated and taken up in $CH_2Cl_2$ (1000 ml). The precipitate is filtered and the filtrate is recovered, dried and evaporated. The product is purified by passage through a silica column (eluant: $CH_2Cl_2$) and recrystallized in a mixture of ethyl acetate (90%) and THF (10%), yielding 8 g (90%) of the methyl ester of 6-[3-(1-adamantyl)-4-methoxyphenyl]-1-methyl-2-naphthoic acid. Melting point: 238°-239° C.

EXAMPLE 22

6-[3-(1-adamantyl)-4-methoxyphenyl]-1-methyl-2-naphthoic acid

Compound of Formula I wherein $R_4=CH_3$, $R_5=H$, $R_2=$1-adamantyl, $R_3=OCH_3$ and $R_1=COOH$ 6.8 g (15.4 mmol) of the ester obtained in Example 21(c) are treated as in Example 10 to give 5.8 g (88%) of the corresponding acid. Melting point: 300°-302° C.

EXAMPLE 23

6-[3-(1-adamantyl)-4-methoxyphenyl]-2-naphthalene methanol

Compound of Formula I wherein $R_4=R_5=H$, $R_2=$1-adamantyl, $R_3=OCH_3$ and $R_1=$—$CH_2OH$ 1.3 g (3 mmol) of the ester obtained in Example 9 dissolved in THF (5 ml) are treated with 171 mg (4.5 mmol) of $LiAlH_4$. The mixture is heated at reflux, cooled and treated with a saturated aqueous solution of the double tartrate of sodium and potassium. The reaction mixture is filtered, evaporated to dryness, and the residue is recrystallized in cyclohexane, yielding 1.0 g (83%) of the 6-[3-(1-adamantyl)-4-methoxyphenyl]-2-naphthalene methanol. Melting point: 163°-164° C.

EXAMPLE 24

Ethylamide of 6-[3-(1-adamantyl)-4-methoxyphenyl]-2-naphthoic acid

Compound of Formula I wherein $R_4=R_5=H$, $R_2=$1-adamantyl, $R_3=OCH_3$ and $R_1=CONHC_2H_5$ (a) 6-[3-(1-adamantyl)-4-methoxy phenyl]-2-naphthoic acid chloride 4.75 g (1.15 mmol) of the acid obtained in Example 10 in 200 ml of dichloromethane are treated with 2.08 g (2.3 ml, 1.15 mmol) of dicyclohexamine. The mixture is stirred at ambient temperature until dissolution. The solvents are evaporated and the residue taken up in ether. The solid thus formed is filtered (6.8 g) and then taken up in methylene chloride (50 ml). 1.37 g (0.84 ml, 1.15 mmol) of thionyl chloride are added. The salt formed is filtered and the filtrate is recovered, evaporated and dried. The resulting solid (3.9 g) is used as such in the following step.

(b) Ethylamide of 6-[3-(1-adamantyl)-4-methoxyphenyl]-2-naphthoic acid 1.3 g (3 mmol) of the acid chloride produced in (a) above are dissolved in 20 ml of THF. 405 mg (600 μl, 9 mmol) of ethylamine are added and the mixture is stirred for 2 hours at ambient temperature. The mixture is then poured into water, extracted with $CH_2Cl_2$, dried and evaporated. The residue is recrystallized in ethyl acetate, yielding 1.1 g (85%) of the expected ethylamide. Melting point: 220°-221° C.

EXAMPLE 25

Morpholide of 6-[3-(1-adamantyl)-4-methoxyphenyl]-2-naphthoic acid

In a manner analogous to Example 24, starting with 1.3 g of acid chloride produced in part (a) of Example 24 and 780 mg (780 ml, 9 mmol) of morpholine, there are obtained 1.3 g (91%) of the expected morpholide. Melting point: 212°-213° C.

EXAMPLE 26

Methyl ester of 6-[3-tert.butyl-4-methoxy phenyl]-2-naphthoic acid

Compound of Formula II wherein $R'_2$=tert.butyl, $R'_3$=$R'_6$=$OCH_3$ (a) 4-bromo-2-tert.butyl anisole 3.10 g (22.6 mmol) of aluminum chloride are added all at once to a mixture of 63.5 g (339 mmol) of p-bromoanisole and 31.4 g (330 mmol) of tert.butyl chloride. The mixture is stirred at ambient temperature until the evolution of gas ceases (about 15 minutes). The mixture is then heated at 80° C. for 15 minutes and poured into ice. 300 ml of water are added and the mixture is extracted with ether.

The organic phase is dried (MgSO₄), the solvents evaporated and the residue purified by chromatography on a silica column (eluant: mixture of methylene chloride-10% and hexane-90%). After evaporation of the solvents, 4-bromo-2-tert.butyl anisole under the form of a colorless oil which crystallized on cooling is obtained. 31.9 g (39%).

(b) Methyl ester of 6-[3-tert.butyl-4-methoxy phenyl]-2-naphthoic acid

There is slowly added, drop by drop, a solution of 18.8 g (77 mmol) of 4-bromo-2-tert.butyl anisole to 2.26 g (93 mmol) of magnesium turnings and a crystal of iodine. The mixture is heated until the Grignard begins to form, at which point the remainder of the solution containing the brominated derivative is poured in a manner to maintain a regular reflux. Once the addition is complete, the mixture is heated at 40° C. for 30 minutes, diluted with 200 ml of THF and cooled to ambient temperature. 12.7 g (93 mmol) of dry zinc chloride in solution in 20 ml of THF are added and the mixture is stirred for 30 minutes at ambient temperature. There are then successively added 12.1 g (46 mmol) of methyl 6-bromo-2-naphthoate and 300 mg of NiCl₂/DPPE complex.

The mixture is stirred for 10 hours at ambient temperature. 300 ml of water are added and the THF is evaporated. The remainder is extracted with methylene chloride. The organic phase is dried (MgSO₄), filtered, evaporated and purified by passage through a silica column (eluant: mixture of 50% dichloromethane and 50% hexane). After evaporation of the solvents, the resulting residue is recrystallized in hexane to give the expected ester: 11.5 g (72%). Melting point: 160° C.

EXAMPLE 27

6-(3-tert.butyl-4-methoxyphenyl)-2-naphthoic acid

Compound of Formula II wherein $R'_2$=tert.butyl, $R'_3$=$OCH_3$ and $R'_6$=OH

In a manner analogous to Example 15, starting with 7.0 g (20 mmol) of the ester obtained in Example 26, 6.0 g (90%) of the expected acid are obtained. Melting point: 268° C.

EXAMPLE 28

Methyl ester of 6-[3-(1,1-dimethyldecyl)-4-methoxyphenyl]-2-naphthoic acid

Compound of Formula I wherein $R_4$=$R_5$=H, $R_2$=$C(CH_3)_2C_9H_{19}$, $R_3$=$OCH_3$ and $R_1$=$COOCH_3$ A solution of 16 g (45 mmol) of 2-(1,1-dimethyldecyl)-4-bromo anisole in 60 ml of THF is slowly added to 1.3 g (54 mmol) of magnesium and a crystal of iodine. The mixture is slightly heated at the beginning of the addition until the reaction of formation of the Grignard is initiated. Then the remainder of the solution containing the brominated derivative is added in a manner to maintain a regular reflux. Once the addition is complete, the mixture is stirred for 30 minutes at 50° C. and then cooled to ambient temperature. 7.4 g (54 mmol) of zinc chloride in solution in 50 ml of THF are added. The mixture is stirred for 30 minutes at ambient temperature, 6.6 g (25 mmol) of methyl 6-bromo-2-naphthoate are added and then 175 mg of NiCl₂/DPPE complex. The mixture is stirred for 3 hours at ambient temperature at which point 250 ml of water are added. The THF is evaporated under reduced pressure and the residue is extracted with dichloromethane, dried and the solvent evaporated. The residue is purified by passage through a silica column (eluant: mixture of 60% dichloromethane and 40% hexane). On evaporation, a solid is obtained which is recrystallized twice in hexane to give the methyl ester of 6-[3-(1,1-dimethyldecyl)-4-methoxyphenyl]-2-naphthoic acid: 7.05 g (61%). Melting point: 92° C.

EXAMPLE 29

6-[3-(1,1-dimethyldecyl)-4-methoxyphenyl)-2-naphthoic acid

Compound of Formula I wherein $R_4$=$R_5$=H, $R_2$=$C(CH_3)_2C_9H_{19}$, $R_3$=$OCH_3$ and $R_1$=COOH In a manner analogous to Example 15, starting with 3.6 g of the ester obtained in Example 28, 3 g (87%) of 6-[3-(1,1-dimethyldecyl)-4-methoxyphenyl]-2-naphthoic acid are obtained. Melting point: 180° C.

EXAMPLES OF COMPOSITIONS

| Example A - Fatty cream wherein the active principle is in suspension | |
|---|---|
| 6-[3-(10-adamantyl)-4-methoxy phenyl]-2-naphthoic acid | 0.001 g |
| A combination of nonionic E/H emulsifiers and a fatty body of mineral origin sold by Goldschmidt under the trade name "Protegin X" | 25.00 g |
| Petrolatum oil | 10.00 g |
| Preservatives, sufficient amount | |
| Water, sufficient amount for | 100.00 g |

In that example, the active compound can be replaced by the same amount of 6-[3-(1-adamantyl)-4-methoxy phenyl]-1-methyl-2-2-naphthoic acid.

| Example B - Skin cream - A fluid cream wherein the active principle is in suspension | |
|---|---|
| Methyl ester of 6-(4-tert.butyl phenyl)-2-naphthoic acid | 0.02 g |
| Sorbitan stearate polyoxyethylenated with 20 moles of ethylene oxide sold by Atlas under the trade name "Tween 60" | 5.00 g |
| Sorbitan monostearate sold by Atlas under the trade name "Span 60" | 2.00 g |
| Cetyl alcohol | 5.00 g |
| Triglycerides of capric and caprylic acids sold by Dynamit Nobel under the trade name "Miglyol 812" | 10.00 g |
| Preservatives, sufficient amount | |
| Water, sufficient amount for | 100.00 g |

| Example C - Gel for the skin or scalp wherein the active principle is in suspension. | |
| --- | --- |
| Methyl ester of 6-(4-t.butyl phenyl)-2-naphthoic acid | 0.10 g |
| Ethanol | 20.00 g |
| Hydroxypropyl cellulose, sold by Hercules under the trade name "Klucel HF", Preservative, sufficient amount | 2.00 g |
| Water, sufficient amount for | 100.00 g |

| Example D - Lotion for the skin | |
| --- | --- |
| 6-[3-(1-adamantyl)-4-methoxyphenyl]-1-methyl-2-naphthoic acid | 0.1 g |
| Polyethylene glycol 400 | 70.0 g |
| Ethanol | 29.9 g |

In that example, the active compound can be replaced by the same amount of 6-[3-(1-adamantyl)-4-methoxyphenyl]-2-naphthoic acid.

| Example E - Unguent for the skin | |
| --- | --- |
| 6-[(3-(1-adamantyl)-4-methoxyphenyl]-2-naphthoic acid | 0.001 g |
| Lanolin | 50 g |
| Vaseline, sufficient amount for | 100 g |

| Example F - Oral composition - 0.30 g gelule. | |
| --- | --- |
| 6-[3-(1-adamantyl)-4-methoxy phenyl]-2-naphthoic acid | 0.003 g |
| Cornstarch | 0.060 g |
| Lactose, suffcient amount for | 0.300 g |

The resulting powder is packaged in a gelule whose wall is made of gelatin, TiO₂ and a preservative.

| Example G - Capsule containing 0.400 g of the following suspension | |
| --- | --- |
| Ethylamide of 6-[3-(1-adamantyl)-4-methoxyphenyl]-2-naphthoic acid | 0.005 g |
| Glycerine | 0.200 g |
| Sucrose | 0.050 g |
| Polyethylene glycol 400 | 0.050 g |
| Purified water, sufficient amount for | 0.400 g |

This suspension is packaged in a capsule made of gelatin, glycerine titanium dioxide and water.

What is claimed is:

1. A benzonaphthalene compound of the formula

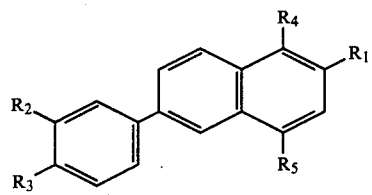

wherein
R₁ represents (i)

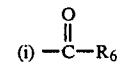

or (ii) —CH₂OH,
R₆ represents

wherein r' and r" represent hydrogen, lower alkyl, mono or polyhydroxyalkyl, aryl or a residue of an amino sugar selected from the group consisting of glucosamine, galactosamine and mannosamine, R₂ represents hydrogen, branched or straight chain alkyl having 1-15 carbon atoms, alkoxy having 1-4 carbon atoms or a cycloaliphatic radical, R₃ represents hydrogen, hydroxy, branched or straight chain alkyl having 1-4 carbon atoms, alkoxy having 1-10 carbon atoms, a cycloaliphatic radical selected from the group consisting of 1-methyl cyclohexyl and 1-adamantyl, a thiocycloaliphatic radical, or —O—Si(CH₃)₂—R₈ wherein R₈ represents linear or branched lower alkyl, and R₄ and R₅ each independently represent hydrogen, lower alkyl, hydroxy or lower acyloxy,
or a salt thereof.

2. The compound of claim 1 having the formula

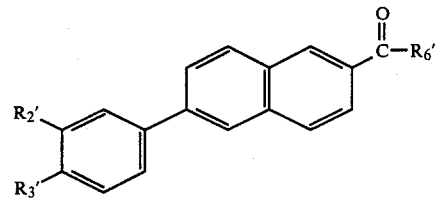

wherein
R'₆ represents

r' and r" each independently represent hydrogen or lower alkyl having 1-6 carbon atoms, R'₂ represents hydrogen, alkyl having 1-15 carbon atoms, alkoxy having 1-4 carbon atoms or 1-adamantyl, and R'₃ represents hydrogen, hydroxy, alkoxy having 1-10 carbon atoms, alkyl having 1-4 carbon atoms or 1-adamantyl thio.

3. The compound of claim 1 selected from the group consisting of
6-[3-(1-adamantyl)-4-methoxyphenyl]-2-naphthalene methanol and
the ethylamide of 6-[3-(1-adamantyl)-4-methoxyphenyl]-2-naphthoic acid.

4. The compound of claim 1 wherein said alkyl is selected from the group consisting of methyl, ethyl, isopropyl, butyl and tert.butyl.

5. The compound of claim 1 wherein said alkoxy is selected from the group consisting of methoxy, ethoxy, isopropoxy, hexyloxy and decyloxy.

6. The compound of claim 1 wherein said lower acyloxy has 1–4 carbon atoms.

7. The compound of claim 6 wherein said lower acyloxy is selected from the group consisting of acetyloxy and propionyloxy.

8. The compound of claim 1 wherein said monohydroxyalkyl has 2 or 3 carbon atoms.

9. The compound of claim 8 wherein said monohydroxyalkyl is selected from the group consisting of 2-hydroxyethyl and 2-hydroxypropyl.

10. The compound of claim 1 wherein said polyhydroxyalkyl has 3–6 carbon atoms and 2–5 hydroxy groups.

11. The compound of claim 10 wherein said polyhydroxyalkyl is selected from the group consisting of 2,3-dihydroxypropyl,
1,3-dihydroxypropyl or a residue of pentaerythritol.

12. The compound of claim 1 wherein said thiocycloaliphatic radical is 1-adamantylthio.

13. A benzonaphthalene compound of the formula

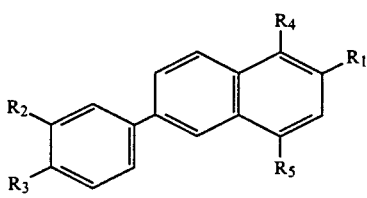

wherein
$R_1$ represents

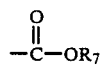

wherein $R_7$ represents hydrogen, alkyl having 1–20 carbon atoms, monohydroxyalkyl or polyhydroxyalkyl, $R_2$ represents hydrogen, branched or straight chain alkyl having 1–15 carbon atoms or alkoxy having 1–4 carbon atoms, $R_3$ represents hydrogen, hydroxy, branched or straight chain alkyl having 1–4 carbon atoms, alkoxy having 1–10 carbon atoms, or $-O-Si(CH_3)_2-R_8$ wherein $R_8$ represents linear or branched alkyl, $R_4$ and $R_5$ each independently represent hydrogen, lower alkyl or lower acyloxy, or a salt thereof.

14. The compound of claim 13 selected from the group consisting of
6-(3-methylphenyl)-2-naphthoic acid,
the methyl ester of 6-(3-methylphenyl)-2-naphthoic acid,
6-(4-tert.butyl phenyl)-2-naphthoic acid,
the methyl ester of 6-(4-tert.butyl phenyl)-2-naphthoic acid,
6-(3-tert.butyl phenyl)-2-naphthoic acid,
the methyl ester of 6-(3-tert.butyl phenyl)-2-naphthoic acid,
6-(3,4-dimethoxy phenyl)-2-naphthoic acid,
the methyl ester of 6-(3,4-dimethoxy phenyl)-2-naphthoic acid,
the methyl ester of 6-(3-tert.butyl-4-methoxyphenyl)-2-naphthoic acid,
6-(3-tert.butyl-4-methoxy phenyl)-2-naphthoic acid,
the methyl ester of 6-[3-(1,1-dimethyldecyl)-4-methoxyphenyl]-2-naphthoic acid and
6-[3-(1,1-dimethyldecyl)-4-methoxyphenyl]-2-naphthoic acid.

15. A pharmaceutical composition comprising a pharmaceutically acceptable vehicle suitable for enteral, parenteral, topical or ocular administration and an effective amount of as the active principle at least one compound of claim 1 or a salt thereof.

16. The pharmaceutical composition of claim 15 wherein said active principle is present in an amount ranging from 0.0005 to about 5 weight percent based on the total weight of said composition.

17. A pharmaceutical composition comprising a pharmaceutically acceptable vehicle suitable for enteral, parenteral, topical or ocular administration and an effective amount of, as the active principle, at least one compound of claim 13 or a salt thereof.

18. The pharmaceutical composition of claim 17 wherein said active principle is present in an amount ranging from 0.0005 to about 5 weight percent based on the total weight of said composition.

* * * * *